United States Patent
Zhu et al.

(10) Patent No.: US 10,443,057 B2
(45) Date of Patent: Oct. 15, 2019

(54) MULTI-TARGETS INTERFERING RNA MOLECULES AND THEIR APPLICATIONS

(71) Applicant: Biomics Biotechnologies Co., Ltd., Nantong (CN)

(72) Inventors: York Yuan Yuan Zhu, Palo Alto, CA (US); Tiejun Li, Nantong (CN)

(73) Assignee: Biomics Biotechnologies, Co., Ltd., Nantong (CN)

( * ) Notice: Subject to any disclaimer, the term of this patent is extended or adjusted under 35 U.S.C. 154(b) by 29 days.

(21) Appl. No.: 14/805,746

(22) Filed: Jul. 22, 2015

(65) Prior Publication Data

US 2016/0053267 A1  Feb. 25, 2016

Related U.S. Application Data

(62) Division of application No. 13/415,600, filed on Mar. 8, 2012, now Pat. No. 9,115,167.

(30) Foreign Application Priority Data

Mar. 10, 2011  (CN) .......................... 2011 1 0056947
Mar. 10, 2011  (CN) .......................... 2011 1 0056948
Mar. 10, 2011  (CN) .......................... 2011 1 0056949

(51) Int. Cl.
*C12N 15/113* (2010.01)
*A61K 31/7088* (2006.01)
*C07H 21/02* (2006.01)

(52) U.S. Cl.
CPC ...... *C12N 15/1135* (2013.01); *A61K 31/7088* (2013.01); *C07H 21/02* (2013.01); *C12N 15/113* (2013.01); *C12N 2310/111* (2013.01); *C12N 2310/14* (2013.01); *C12N 2310/3519* (2013.01); *C12N 2310/52* (2013.01); *C12N 2310/53* (2013.01); *C12N 2310/531* (2013.01)

(58) Field of Classification Search
None
See application file for complete search history.

(56) References Cited

U.S. PATENT DOCUMENTS

| | | | | |
|---|---|---|---|---|
| 9,200,276 B2 * | 12/2015 | Hauser | | C12N 15/111 |
| 2004/0086911 A1 * | 5/2004 | Cabello | | C12N 15/111 |
| | | | | 435/6.14 |
| 2006/0035344 A1 | 2/2006 | Pachuk et al. | | |
| 2006/0084621 A1 * | 4/2006 | Vornlocher | | C12N 15/113 |
| | | | | 514/44 A |
| 2008/0214489 A1 * | 9/2008 | Keefe | | C12Y 207/11013 |
| | | | | 514/44 R |
| 2009/0126038 A1 * | 5/2009 | Van De Craen | | C12N 15/111 |
| | | | | 800/278 |
| 2010/0093085 A1 | 4/2010 | Yamada et al. | | |
| 2010/0137407 A1 | 6/2010 | Abe et al. | | |
| 2011/0008885 A1 | 1/2011 | Kim et al. | | |
| 2011/0159586 A1 * | 6/2011 | Hauser | | A61K 31/70 |
| | | | | 435/375 |
| 2012/0184598 A1 * | 7/2012 | Hauser | | C12N 15/111 |
| | | | | 514/44 A |

FOREIGN PATENT DOCUMENTS

| | | |
|---|---|---|
| CN | 102191246 A | 9/2011 |
| WO | 2009008645 A2 | 1/2009 |
| WO | WO2009/076321 * | 6/2009 |
| WO | WO2010/141511 * | 12/2010 |

OTHER PUBLICATIONS

Svoboda, et al. (2006) "Hairpin RNA: A Secondary Structure of Primary Importance". Cell. Mol. Life Sci. v.63:901-18.*
The DINAMelt Web Server [online]. [Retrieved on Oct. 24, 2017]. Retrieved from the Internet: <http://unafold.rna.albany.edu/?q=DINAMelt/Two-state-melting>.*
The DINAMelt Web Server [online]. [Retrieved on Mar. 4, 2019]. Retrieved from the Internet: <http://unafold.rna.albany.edu/?q=DINAMelt/Two-state-melting>.T (Year: 2019).*
Ren et al. (2009) Cancer Letters: 281:134-43.

* cited by examiner

*Primary Examiner* — Jennifer Pitrak McDonald
(74) *Attorney, Agent, or Firm* — Fox Rothschild LLP

(57) ABSTRACT

This invention relates to interfering RNA (iRNA) molecules and their applications, especially multi-targets iRNA molecules and their applications. The said multi-targets iRNA molecules comprised of a sense strand annealed onto at least one antisense strand, each strand is at least 30 nucleotides in length, the sense or antisense strand has at least two segments, which can target at least two RNAs of different genes, or can target at least two portions of an RNA, and wherein the iRNA does not induce an interferon-response when transfected into a cell. The iRNA molecule can interfere with the translation procedure post-transcription, and the target gene is inhibited or blocked, the iRNA does not induce an interferon-response in vivo. The RNA molecules are the active ingredient in preparation of the drug which can regulate one or many genes function.

6 Claims, 9 Drawing Sheets

Specification includes a Sequence Listing.

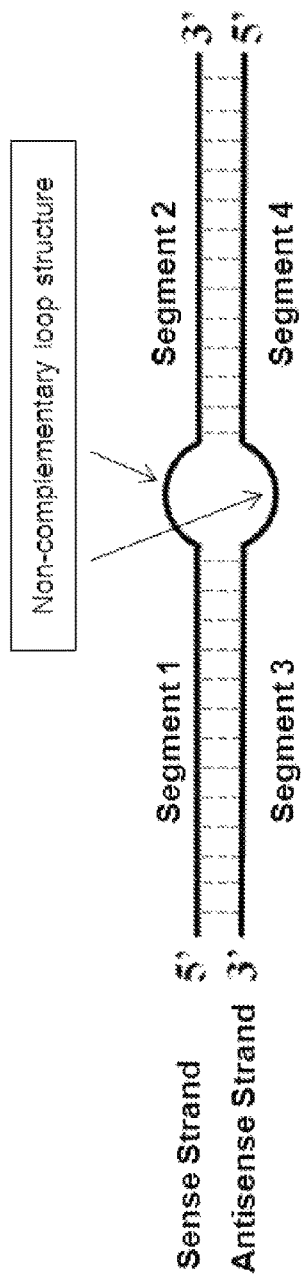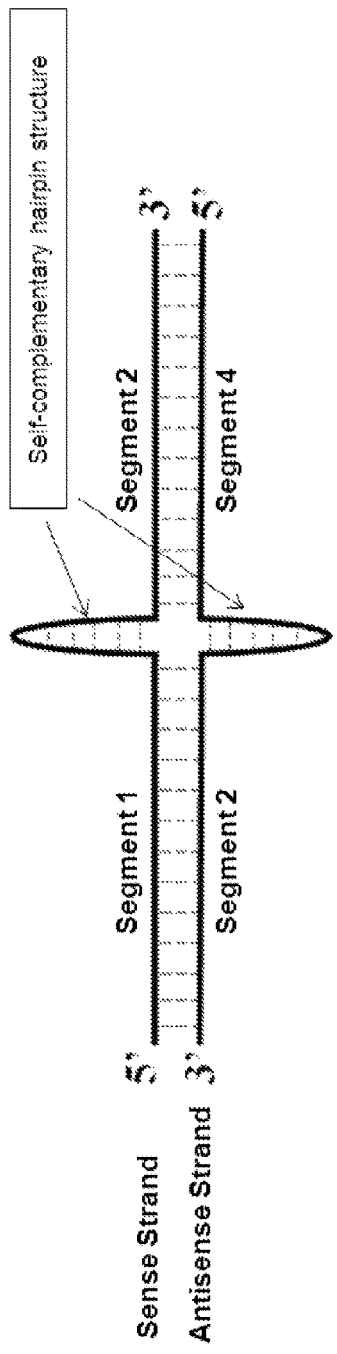

SEQUENCE LISTING

<160> NUMBER OF SEQ ID NOS: 13

<210> SEQ ID NO 1
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gacuuggccc aguguuucuu caggaugacu gaguaccuga a                                41

<210> SEQ ID NO 2
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uucagguacu cagucauccg agagaaacac ugggccaagu c                                41

<210> SEQ ID NO 3
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gacuuggccc aguguuucuc augcgucggg augacugagu accugaa                          47

<210> SEQ ID NO 4
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uucagguacu cagucauccg cagcacacag aaacacuggg ccaaguc                          47

<210> SEQ ID NO 5
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gacuuggccc aguguuucuc augcgucggg augacugagu accugaa                          47

<210> SEQ ID NO 6
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uccuuucugu caagaagcag uucagaaaca cugggccaag uc                               42

```
<210> SEQ ID NO 7
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uucagguacu cagucauccc aacugcuucu ugacagaaag ga                    42

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
accgcatctc tacattcaag                                             20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caagtctggc tcgttctc                                               18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggctgggatg cctttgtg                                               18

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gccaggagaa atcaaacaga gg                                          22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtgagctcct ggattctgct                                             20
```

```
<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgttccaatg taaccatatt tctga                                            25
```

MULTI-TARGETS INTERFERING RNA MOLECULES AND THEIR APPLICATIONS

CROSS-REFERENCE

This application is a Divisional application of U.S. patent application Ser. No. 13/415,600, filed Mar. 8, 2012, which claims the benefit of Chinese Application Nos. 201110056947.0, 201110056948.5, and 201110056949.X, all filed Mar. 10, 2011. The contents of all applications are hereby incorporated by reference in their entirety.

BACKGROUND OF THE INVENTION

RNA interference (RNAi) is a form of post-transcriptional gene silencing in which double-stranded RNA (dsRNA) induces the enzymatic degradation of homologous messenger RNA (mRNA). When a long dsRNA enters a cell, an enzyme called Dicer binds and cleaves the long dsRNA. Cleavage by Dicer results in the production of a small interfering RNA (siRNA) that is generally 20-25 base pairs (bp) in length and has a 2-nucleotide long 3' overhang on each strand. One of the two strands of each siRNA, generally the antisense strand, is then incorporated into an RNA-induced silencing complex (RISC), and pairs with complementary RNA sequences. RISC first mediates the unwinding of the siRNA duplex, a single-stranded siRNA that is coupled to RISC, then binds to a target mRNA in a sequence-specific manner. The binding mediates target mRNA cleavage by Slicer, an argonaute protein that is the catalytic component of RISC. Cleavage of the mRNA prevents translation from occurring, which prevents the ultimate expression of the gene from which the mRNA is transcribed. Now, it has been confirmed that RNAi has great potential treatment of a variety viral infections, and it is the ideal treatment for blocking gene expression.

RNAi has tremendous potential in medicinal therapeutics, such as in anti-viral, oncogenic and anti-inflammatory applications. The double-stranded siRNA may be a long double-strand designed to be cleaved by Dicer, called Dicer substrate, or it may be short and is designed to bypass Dicer serve directly as a RISC substrate. The dsRNAs are synthesized with a sequence complementary to a gene of interest and introduced into a cell or organism, where they are recognized as exogenous genetic materials and activate the RNAi pathway. RNAi can cause a drastic decrease in the expression of a targeted gene by using this mechanism.

RNAi can be used to develop a whole new class of therapeutics. Currently there are more than ten kinds of siRNA drug at the clinic stage. Among the applications to reach clinical trials are treatment of age-related macular degeneration, diabetic retinopathy, and respiratory syncytial virus, solid tumors, liver cancer, and acute kidney injury and other diseases.

SUMMARY OF THE INVENTION

The present application provides compounds and processes related to interfering RNA (iRNA) molecules and applications thereof. The iRNA molecule having antisense strand that can target or hybridize to RNAs of two or more different target genes or two or more different sites of a RNA of a single target gene. The RNAs could be mRNA, microRNA (miRNA) or two or more subsequences of one mRNA or miRNA, and which does not induce an interferon response.

The present invention further provides a multiple targets iRNA having a sense strand and at least one antisense strand. The length of each strand is at least 30, 31, 32, 33, 34, 35, 36, 40, or more nucleotides, the sense or antisense strand can target at least two different RNAs or two different sequences on a single RNA.

Generally, the iRNA comprises a non-complementary loop structure or a self-complementary hairpin structure, and wherein the iRNA does not induce an interferon-response when introduced (e.g. by transfection) into a cell.

Preferably, the non-complementary loop structure contains at least 3 nucleotides, and the self-complementary hairpin structure contains at least 7, 8, 9, 10, 11, 12, 13, 14, 15, or more nucleotides.

Preferably, the iRNA comprises a nucleotide with sugar or backbone modification.

Usually, the iRNA comprise a sense and a antisense strand or two antisense strands, all independently with a length that is at least 30, 31, 32, 33, 34, 35, 36, 40, or more nucleotides long, and the double-stranded iRNA contains at least a non-complementary loop structure and a self-complementary hairpin structure, and the iRNA does not induce an interferon-response when introduced into a mammalian cell.

The invention also discloses the applications of the iRNAs in the gene modulation drugs preparation, and the drug modulates at least one gene. The gene is a disease-related gene, includes pathogen gene, such as viral gene, and non-infectious disease gene, such as cancer gene and etc. The cancers is liver cancer, lung cancer, gastric carcinoma, cervical cancer, multiple myeloma, cutaneous squamous cell carcinoma, colon carcinoma, melanoma, bladder carcinoma, osteosarcoma, nasopharyngeal carcinoma, or mouth cancer, and the like.

The composition of the present invention is used to suppress, mitigate or reduce the symptoms of the disease or prevent the recurrence of certain diseases.

The present invention provides iRNA that can inhibit expression of multiple target genes, or target multiple sites of the same gene. In addition, it does not induce an interferon-response, can be applied to mammalian cells. The disclosed RNA molecule is a new siRNA application form with a broad range of applications in gene therapy for diseases.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which.

FIG. 1 shows the structure of Mid-Cir. The molecule has segment 1 of a sense strand which is complementary to segment 3 of an antisense strand. Segment 2 of the sense strand is complementary to the segment 4 of the antisense strand. Mid-Cir has a non-complementary loop structure in both the sense and the antisense strands.

FIG. 2 shows the structure of Mid-Loop. The molecule has segment 1 of a sense strand which is complementary to segment 3 of an antisense strand. Segment 2 of the sense strand is complementary to segment 4 of the antisense strand. Mid-Loop has a self-complementary hairpin structure in both the sense and the antisense strands.

DETAILED DESCRIPTION OF THE INVENTION

Figure 3:
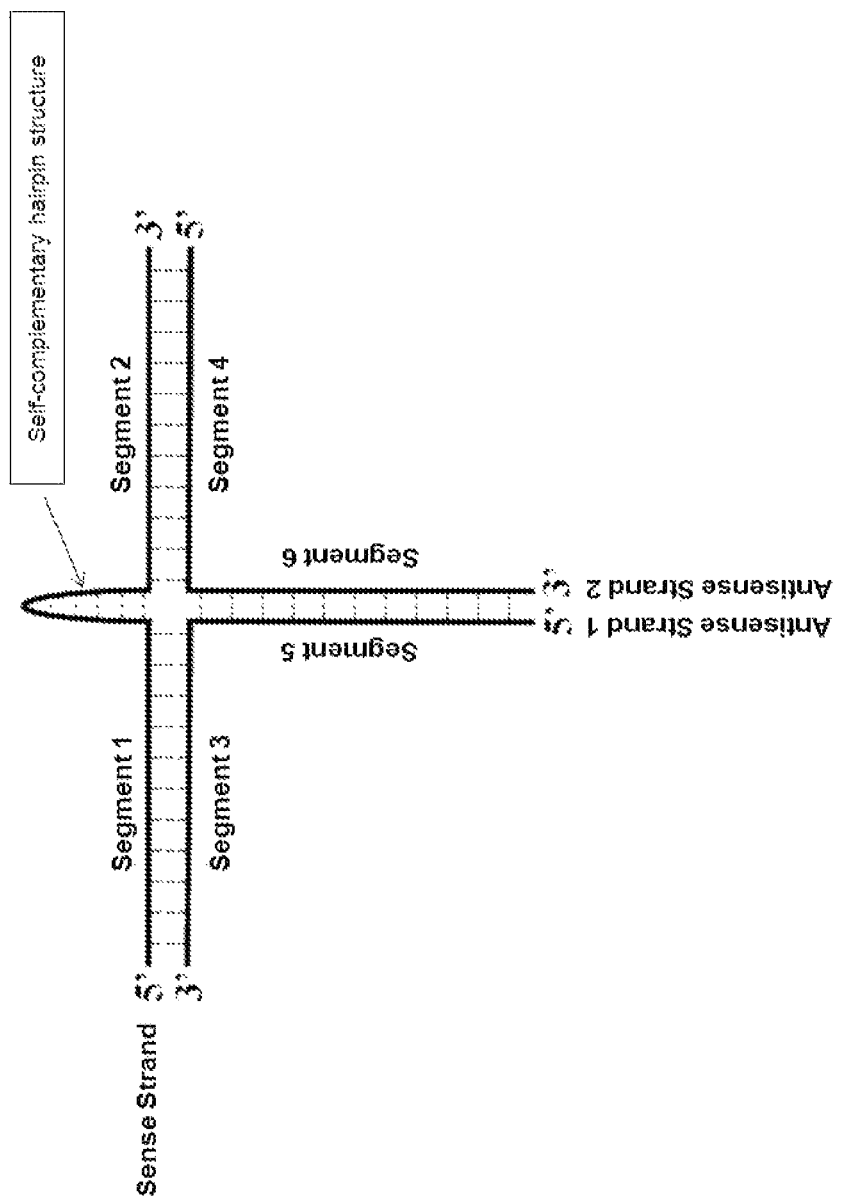
FIG. 3 shows the structure of By-Pass. The molecule has a sense strand annealed onto two antisense strands, each strand has two segments (a 5' segment and a 3' segment). The 5' segment (segment 1) of the sense strand is complementary to the 3' segment (segment 3) of the first antisense strand (antisense strand 1). The 3' segment (segment 2) of the sense strand is complementary to the 5' segment (segment 4) of the second antisense strand (antisense strand 2). The 5' segment (segment 5) of the first antisense strand (antisense strand 1) is complementary to the 3' segment (segment 6) of the second antisense strand (antisense strand 2). After annealing of the three strands, a shelf-complementary hairpin structure is formed in the sense strand.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

I. Multi-Target RNAs

In one aspect, the present invention provides compositions and methods related to an iRNA for targeting RNAs of different genes or different region of an RNA of a single gene.

In mammalian cells, long dsRNA induces interferon response easily, therefore for application of RNAi in mammalians, the length of siRNA is generally be shorter than 30 bps. Nevertheless, long interfering RNA is useful for many applications. Long interfering RNA can contain multiple targeting sequences, and thus can target multiple mRNAs of different target genes or more than one site of the same mRNA of a single gene. Multi-target iRNA can increase gene silencing effect and expand the range of applications.

The development of diseases is complex biological processes with many genes participate, and is affected by many factors. In the treatment of diseases single-target treatment has its limitations Inhibition of a single gene generally cannot completely suppress or reverse the development of diseases. Thus, it is necessary to research and develop long interference nucleic acids that are double-stranded, have multiple targets, have no interferon response, and can suppress multiple disease genes expression. It can improve the therapeutic efficacy and be used as new ways of treating diseases.

By "multi-target iRNA" herein is meant a RNA that targets different RNAs of different target genes or different sites of one target RNA of a single target gene. Multi-target iRNA can be used to modulate the expression of one or more target genes.

"Target" or "target gene" refers to a gene whose expression is selectively inhibited or "silenced." This silencing is achieved by cleaving or translationally silencing or enhance RNA degradation of the mRNA of the target gene (also referred to herein as the "target mRNA") by an iRNA, or an RNA silencing agent, e.g., an siRNA synthesized enzymatically or non-enzymatically, or created from an engineered RNA precursor by a cell's RNA silencing system.

"RNA silencing agent" refers to an RNA (or analog thereof), having sufficient sequence complementarity to a target RNA (i.e., the RNA being degraded) to direct RNA silencing (e.g., RNAi). An RNA silencing agent having a "sequence sufficiently complementary to a target RNA sequence to direct RNA silencing" means that the RNA silencing agent has a sequence sufficient to trigger the destruction or post-transcriptional silencing of the target RNA by the RNA silencing machinery (e.g., the RISC) or related process. An RNA silencing agent having a "sequence sufficiently complementary to a target RNA sequence to direct RNA silencing" also means that the RNA silencing agent has a sequence sufficient to trigger the translational inhibition of the target RNA by the RNA silencing machinery or process.

As used herein, the term multiple targets refers to the antisense strand of the interfering RNA (iRNA) targeting different RNAs of different target genes or different sites of one target RNA of a single gene. The RNA could be mRNA, microRNA (miRNA) or two or more subsequences of one mRNA or miRNA.

By "modulation" or "modulation of expression" herein is meant either an increase (stimulation) or a decrease (inhibition) in the amount or levels of a nucleic acid molecule encoding the gene, e.g., DNA or RNA Inhibition is often the preferred form of modulation of expression and mRNA is often a preferred target nucleic acid.

Modified nucleotides in an iRNA molecule can be in the antisense strand, the sense strand, or both.

In some embodiments, iRNA molecules comprise separate sense and antisense sequences or regions, wherein the sense and antisense regions are covalently linked by nucleotide or non-nucleotide linker molecules, or are non-covalently linked by ionic interactions, hydrogen bonding, van der Waals interactions, hydrophobic interactions, and/or stacking interactions.

The RNA molecules can be assembled from two separate oligonucleotides into a duplex, where one strand is the sense strand and the other is the antisense strand, wherein the antisense and sense strands are base complementary. The antisense strand may comprise a nucleotide sequence that is complementary to a nucleotide sequence in a target nucleic acid or a portion thereof, and the sense strand may comprise a nucleotide sequence corresponding to the target nucleic acid sequence or a portion thereof.

The use herein of the term "Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides.

By "RNA" herein is meant a molecule comprising at least one ribonucleotide residue. By "ribonucleotide" is meant a nucleotide with a hydroxyl group at the 2' position of a beta D-ribo-furanose moiety. The terms include double-stranded RNA, single-stranded RNA, isolated RNA such as partially purified RNA, essentially pure RNA, synthetic RNA, recombinant produced RNA, as well as altered RNA that differs from naturally occurring RNA by the addition, deletion, substitution and/or alteration of one or more nucleotides. Such alterations can include addition of non-nucleotide material, such as to the end(s) of the iRNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

As used herein complementary nucleotide bases are a pair of nucleotide bases that form hydrogen bonds with each other. Adenine (A) pairs with thymine (T) or with uracil (U) in RNA, and guanine (G) pairs with cytosine (C). Complementary segments or strands of nucleic acid hybridize (join by hydrogen bonding) with each other.

As used in the invention, the term "non-complementary loop structure" refers to the non-complementary nucleotide sequence which locates in the sense strand with a corresponding sequence in the antisense strand. The length is at least 3 nucleotides and there is no self-complementary sequence in the nucleotide sequence. The sequence forms a looped second structure after the sense and antisense strand have annealed.

Chemical Composition of iRNAs

The iRNA of the present invention comprises single-stranded or double-stranded oligonucleotides.

The term "double-stranded RNA" or "dsRNA", as used herein, refers to a ribonucleic acid molecule, or complex of ribonucleic acid molecules, having a duplex structure including two anti-parallel and substantially complementary, as defined herein, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5'end of the respective other strand forming the duplex structure, the connecting structure is referred to as a "linker." The RNA strands may have the same or a different number of nucleotides. The maximum number of base pairs is the number of nucleotides in the shortest strand of the dsRNA. In addition to the duplex structure, a dsRNA may comprise one or more nucleotide overhangs. A dsRNA as used herein is also referred to as an "iRNA".

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to the corresponding segment of a highly conserved domain sequence of a viral genome sequence. As used herein, the term "region of complementarity" refers to the region on the antisense strand that is substantially complementary to a sequence, for example a target sequence, as defined herein. Where the region of complementarity is not fully complementary to a highly conserved domain sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand. Sense strand generally is the same strand as a RNA transcribed from a viral genome, preferably an RNA encoding a protein.

The term "identity" is the relationship between two or more polynucleotide sequences, as determined by comparing the sequences. Identity also means the degree of sequence relatedness between polynucleotide sequences, as determined by the match between strings of such sequences. While there exist a number of methods to measure identity between two polynucleotide sequences, the term is well known to skilled artisans (see, e.g., Sequence Analysis in Molecular Biology, von Heinje, G., Academic Press (1987); and Sequence Analysis Primer, Gribskov., M. and Devereux, J., eds., M. Stockton Press, New York (1991)). "Substantially identical," as used herein, means there is a very high degree of homology (e.g., 100% sequence identity) between the sense strand of the dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is typical, the dsRNA may contain single or multiple base-pair random mismatches between the RNA and the highly conserved domain sequence.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. In some embodiments, the presence of only one nucleotide overhang strengthens the activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. In one embodiment, the antisense strand of the dsRNA has 1-10 nucleotides overhangs each at the 3' end and the 5' end over the sense strand. In one embodiment, the sense strand of the dsRNA has 1-10 nucleotides overhangs each at the 3' end and the 5' end over the antisense strand. In another embodiment, one or more of the nucleotides in the overhang is replaced with a nucleoside thiophosphate.

In some embodiments, the iRNA comprises RNA:RNA duplex with 0, 1, 2, 3, 4, or 5 base pairs of DNA attached to the 3' end or 5' end of the RNA:RNA duplex. In some embodiments, attachment of the DNA base pairs to the 3'end is preferred. The base pairs can have 1, 2, 3, or 4 nucleotides overhang. In some embodiments, a blunt end DNA base pair is preferred. In some embodiments, the DNA is preferably a T, or dT.

In some embodiments, the iRNA comprises 1, 2, 3, 4, or 5 bases of deoxyribonucleotides at the 3'-end of the nucleotide sequence. The bases can be cytosine (C), guanine (G), adenine (A), uracil (U), deoxycytidine (dC), deoxyguanosine (dG), deoxyadenine (dA), or deoxythymidine (dT), or analogues thereof.

In the context of this invention, the term "oligonucleotide" refers to an oligomer or polymer of ribonucleic acid (RNA) or deoxyribonucleic acid (DNA) or mimetics thereof.

As used herein, the term "oligonucleotide", includes linear or circular oligomers of natural and/or modified monomers or linkages, including deoxyribonucleosides, ribonucleosides, substituted and alpha-anomeric forms thereof, peptide nucleic acids (PNA), linked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hoogsteen types of base pairing, or the like.

The oligonucleotide may be "chimeric", that is, composed of different regions. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques.

In some embodiments, the region of the oligonucleotide which is modified comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. The effect of such increased affinity is to greatly enhance iRNA oligonucleotide inhibition of gene expression. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance.

Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. *Acc. Chem. Res.* 1995, 28:366-374.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG to synthesize fluorescently labeled, biotinylated or other modified oligonucleotides such as cholesterol-modified oligonucleotides.

The antisense and sense strand of the iRNA of the invention could be nucleotide analogues which contain sugar or backbone modification.

In accordance with the invention, use of modifications such as the use of LNA monomers to enhance the potency, specificity and duration of action and broaden the routes of administration of oligonucleotides comprised of current chemistries such as MOE, ANA, FANA, PS etc (ref: Recent advances in the medical chemistry of antisense oligonucleotide by Uhlman, Current Opinions in Drug Discovery & Development 2000 Vol 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 10 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in o Nielsen et al., *Science,* 1991, 254, 1497-1500.

In a more preferred embodiment of the invention the oligonucleotides with phosphorothioate backbones and oligonucleosides with heteroatom backbones, and in particular-$CH_2$—NH—O—$CH_2$—, —$CH_2$—N($CH_3$)—O—$CH_2$- known as a methylene(methylimino) or MMI backbone, —$CH_2$—O—N($CH_3$)—$CH_2$—, —$CH_2$N($CH_3$)—N($CH_3$) $CH_2$— and —O—N($CH_3$)—$CH_2$—$CH_2$— wherein the native phosphodiester backbone is represented as —O—P—O—$CH_2$— of the above referenced U.S. Pat. No. 5,489,677, and the amide backbones of the above referenced U.S. Pat.

No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C to CO alkyl or $C_2$ to CO alkenyl and alkynyl. Particularly preferred are $O[(CH_2)_nO]_m CH_3$, $O(CH_2)_nOCH_3$, $O(CH_2)_nNH_2$, $O(CH_2)_nCH_3$, $O(CH_2)_n ONH_2$, and $O(CH_{2n}ON[(CH_2)_nCH_3)]_2$ where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy(2'-O—$CH_2$ $CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification comprises 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_3)_2$, also described in examples herein below.

Other preferred modifications comprise 2'-methoxy(2'-$OCH_3$), 2'-aminopropoxy(2'-O $CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514, 785; 5,519,134; 5,567,811; 5,576,427; 5,591,722; 5,597,909; 5,610,300; 5,627,053; 5,639,873; 5,646, 265; 5,658,873; 5,670,633; and 5,700,920, each of which is herein incorporated by reference in its entirety.

Oligonucleotides may also comprise nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopaedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications.

Representative United States patents that teach the preparation of the above noted modified nucleobases as well as other modified nucleobases comprise, but are not limited to, U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N. Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Mancharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., *J. Pharmacol. Exp. Ther.,* 1996, 277, 923-937).

Representative United States patents that teach the preparation of such oligonucleotide conjugates comprise, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Sequence of iRNAs

In some embodiments, the nucleotide sequence is at least 85%, 86%, 87%, 88%, 89%, 90%, 91%, 92%, 93%, 94%, 95%, 96%, 97%, 98%, 99%, or 100% identical to a fragment of a target sequence.

In general, a batch of iRNAs is designed and synthesized, preferably includes all the possible iRNAs for a given target gene or target genes.

After one or more lead iRNAs are identified, they can be further optimized by adjusting sequence, structure, modification, etc., to achieve desired characteristics, such as DM and PK.

Characteristics of iRNA include, but are not limited to, stability, efficacy, and toxicity.

The iRNA may also be optimized in conjunction with a delivery system as provided herein, or known in the art.

III. Method of Treatments

In another aspect, the present invention provided a method for treating a disease, comprising administering a pharmaceutically effective amount of the iRNA provided herein to a subject in need of such treatment.

The term "subject," or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the mammal is a human.

The RNA molecule of this invention can be administered in conjunction with RNA transfer vector and other known treatments for a disease condition.

The associated formulations of drugs vary in compliance with the administration of the corresponding diseases and are appropriate to maintain the activity of iRNA molecules. For example, for injectable drug together with proper delivery systems, the formulation can be a lyophilized powder.

Optionally, the above drug formulations can contain any pharmaceutical acceptable adjuvant, as long as the appropriate delivery systems suitable and appropriate to maintain the activity of RNA molecules.

The iRNA molecule of the present invention may be administered in any form, for example transdermally or by local injection.

The compositions of the present invention may also be formulated and used as tablets, capsules or elixirs for oral administration, suppositories for rectal administration, sterile solutions, suspensions for injectable administration, and the other forms known in the art.

In a preferred embodiment, the iRNA comprised of an antisense and a sense strand, the sense and antisense strand annealed into duplex, the duplex contains a non-complementary loop structure. The antisense strand target two and/or more target RNA of genes or two and/or more sites of one target RNA of a target gene, and it does not induce an interferon-response when introduced (e.g. y transfection) into a cell.

IV. Pharmaceutical Compositions and Delivery

In yet another aspect, the present invention provides a pharmaceutical composition, comprising the iRNA of provided herein, and a pharmaceutical acceptable carrier.

The present invention provides the preparation of iRNA molecules to treat pathological angiogenesis-related diseases. The associated formulations of drugs vary in compliance with the administration of the corresponding diseases and are appropriate to maintain the activity of iRNA molecules. For example, for injectable drug together with proper delivery systems, the formulation can be a lyophilized powder.

Optionally, the above drug formulations can contain any pharmaceutical acceptable adjuvant, as long as the appropriate delivery systems suitable and appropriate to maintain the activity of iRNA molecules.

For example, in clinical application of ophthalmic drugs, the iRNA of the present invention can be dissolved in sterile water free of RNA enzymes. The iRNA concentration is adjusted to 1 μg/μL. The intravitreal injection is performed after gentle mixture of the preparation. The injection is conducted once every two weeks, 4 weeks as a course of a treatment.

In another preferred embodiment, treatment of a patient comprises administration one or more of the RNA compounds, in conjunction with other therapies, for example, chemotherapy, radiation, surgery, anti-inflammatory agents and the like. The other agents can be administered, prior to, after or co-administered with the RNA compounds.

The RNA compounds of the invention encompass any pharmaceutically acceptable salts, esters, or salts of such esters, or any other compound which, upon administration to an animal comprising a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bio-equivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salt" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. Pharma Sci.*, 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

As used herein, a "pharmaceutical addition salt" comprises a pharmaceutically acceptable salt of an acid form of one of the components of the compositions of the invention. These comprise organic or inorganic acid salts of the amines. Preferred acid salts are the hydrochlorides, acetates, salicylates, nitrates and phosphates. Other suitable pharmaceutically acceptable salts are well known to those skilled in the art and comprise basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in Nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and comprise alkaline, alkaline earth, ammonium and quaternary ammonium cations. Carbonates or hydrogen carbonates are also possible. For oligonucleotides, preferred examples of pharmaceutically acceptable salts comprise but are not limited to: (I) salts formed with cations such as sodium, potassium, ammonium, magnesium, calcium, polyamides such as spermine and spermidine, and the like; (II) acid addition salts formed with inorganic acids, for example hydrochloric acid, hydrobromic acid, sulfuric acid, phosphoric acid, nitric acid and the like; (III) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (IV) salts formed from elemental anions such as chlorine, bromine, and iodine.

The RNA compounds of the present invention can be utilized for diagnostics, therapeutics, prophylaxis and as research reagents and kits. For therapeutics, an animal, preferably a human, suspected of having a disease or disorder, which can be treated by modulating the expression of a target gene is treated by administering RNA compounds in accordance with this invention. The compounds of the invention can be utilized in pharmaceutical compositions by adding an effective amount of an iRNA compound to a suitable pharmaceutically acceptable diluent or carrier. Use of the RNA compounds and methods of the invention may also be useful prophylactically.

The present invention also comprises pharmaceutical compositions and formulations, which comprise the RNA compounds of the invention. The pharmaceutical compositions of the present invention may be administered in a number of ways depending upon whether local or systemic treatment is desired and upon the area to be treated. Administration may be topical (comprising ophthalmic and to mucous membranes comprising vaginal and rectal delivery), pulmonary, e.g., by inhalation of powders or aerosols, comprising by nebulizer, intratracheal, intranasal, epidermal and transdermal), oral or parenteral.

Pharmaceutical compositions of the present invention comprise, but are not limited to, solutions, emulsions, and liposome-containing formulations. These compositions may be generated from a variety of components that comprise, but are not limited to, preformed liquids, self-emulsifying solids and self-emulsifying semisolids.

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The co-administration of a nucleic acid and a carrier compound, typically with an excess of the latter substance, can result in a substantial reduction of the amount of nucleic acid recovered in the liver, kidney or other extra circulatory reservoirs, presumably due to competition between the carrier compound and the nucleic acid for a common receptor. For example, the recovery of a partially phosphorothioate oligonucleotide in hepatic tissue can be reduced when it is co-administered with polyinosinic acid, dextran sulphate, polycytidic acid or 4-acetamido-4'isothiocyano-stilbene-2,2'disulfonic acid (Miyao et al., *Antisense Res. Dev.,* 1995, 5, 115-121; Takakura et al., *Antisense & Nucl. Acid Drug Dev.,* 1996, 6, 177-183).

Certain embodiments of the invention provide pharmaceutical compositions containing one or more RNA compounds and one or more other chemotherapeutic agents which function by a non-TRL related mechanism.

Examples of such chemotherapeutic agents comprise, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MIX), colchicine, vincristine, vinblastine, etoposide, teniposide, cisplatin and diethylstilbestrol (DES). See, generally, The Merck Manual of Diagnosis and Therapy, 15th Ed., Berkow et al., eds., 1987, Rahway, N.J., pages 1206-1228).

Anti-inflammatory drugs, comprising but not limited to nonsteroidal anti-inflammatory drugs and corticosteroids, and antiviral drugs, comprising but not limited to ribivirin, vidarabine, acyclovir and ganciclovir, may also be combined in compositions of the invention (The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more RNA compounds, particularly iRNAs with different sequences. Two or more combined compounds may be used together or sequentially.

Nucleic Acid Delivery System

Preferred invention practice involves administering at least one of the foregoing RNA oligonucleotides with a suitable nucleic acid delivery system, e.g. as disclosed in US Pat. Appl. Pub. No. 20090247604, the disclosure of which are incorporated by reference in its entirety.

In one embodiment, that system includes a non-viral vector operably linked to the polynucleotide. Examples of such non-viral vectors include the oligonucleotide alone or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutination virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., *J. Neurochem,* 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.: U.S.A.:* 90 7603 (1993); Geller, A. I., et al., Proc Natl. Acad. Sci USA: 87:1149 (1990)], Adenovirus Vectors [LeGal LaSalle et al., *Science,* 259:988 (1993); Davidson, et al., *Nat. Genet.* 3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated.

The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). Promoters are discussed infra. The plasmid vector may also include a selectable marker such as the β-lactamase gene for ampicillin resistance, provided that the marker polypeptide does not adversely effect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques,* 6:682 (1988). See also, Felgner and Holm, *Bethesda Res. Lab. Focus,* 11(2):21 (1989) and Maurer, R. A., *Bethesda Res. Lab. Focus,* 11(2):25 (1989).

Replication-defective recombinant adenoviral vectors can be produced in accordance with known techniques. See, Quantin, et al., *Proc. Natl. Acad. Sci. USA,* 89:2581-2584 (1992); Stratford-Perricadet, et al., *J. Clin. Invest.,* 90:626-630 (1992); and Rosenfeld, et al., *Cell,* 68:143-155 (1992).

Another preferred antisense oligonucleotide delivery method is to use single stranded DNA producing vectors which can produce the antisense oligonucleotides intracellularly. See for example, Chen et al, *BioTechniques,* 34: 167-171 (2003), which is incorporated herein, by reference, in its entirety.

The effective dose of the nucleic acid will be a function of the particular expressed protein, the particular cardiac arrhythmia to be targeted, the patient and his or her clinical condition, weight, age, sex, etc.

One preferred delivery system is a recombinant viral vector that incorporates one or more of the polynucleotides therein, preferably about one polynucleotide. Preferably, the viral vector used in the invention methods has a pfu (plague forming units) of from about $10^8$ to about $5\times10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

Embodiments of the invention also relates to expression vector constructs for the expression of the RNA oligonucleotides which contain hybrid promoter gene sequences and possess a strong constitutive promoter activity or a promoter activity which can be induced in the desired case.

Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for polymerases. Much of the thinking about how promoters are organized derives from analyses of several viral promoters, including those for the HSV thymidine kinase (tk) and SV40 early transcription units. Promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 b.p. upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 b.p. apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tetracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic Virus, HSV-TK, and avian sarcoma virus.

In a preferred embodiment, tissue specific promoters are used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate.

IRES:

In certain embodiments of the invention, the use of internal ribosome entry site (IRES) elements is contemplated to create multigene, or polycistronic, messages. IRES elements are able to bypass the ribosome scanning model of 5' methylated Cap dependent translation and begin translation at internal sites. IRES elements from two members of the picornavirus family (poliovirus and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

Kits

In another aspect, the present invention provides a kit comprises one or more RNA oligonucleotides provided herein. These oligonucleotides can comprise one or more modified nucleobases, shorter or longer fragments, modified bonds and the like. In yet another aspect, the invention provides kits for targeting nucleic acid sequences of cells and molecules associated with modulation of the immune response in the treatment of diseases such as, for example, infectious disease organisms, AMD, angiogenesis related diseases, cancer, autoimmune diseases and the like.

In one embodiment, a kit comprises: (a) an RNA provided herein, and (b) instructions to administer to cells or an individual a therapeutically effective amount of RNA oligonucleotide. In some embodiments, the kit may comprise pharmaceutically acceptable salts or solutions for administering the RNA oligonucleotide. Optionally, the kit can further comprise instructions for suitable operational parameters in the form of a label or a separate insert. For example, the kit may have standard instructions informing a physician or laboratory technician to prepare a dose of RNA oligonucleotide.

Optionally, the kit may further comprise a standard or control information so that a patient sample can be compared with the control information standard to determine if the test amount of RNA oligonucleotide is a therapeutic amount consistent with for example, a shrinking of a tumor.

Embodiments of the invention may be practiced without the theoretical aspects presented. Moreover, the theoretical aspects are presented with the understanding that Applicants do not seek to be bound by the theory presented.

EXAMPLES

It should be understood that the following examples used only to clarify the present invention, but not to limit this invention.

It must be explained, if not specified, that the percentage of following examples are all weight percent content wt %.

Example 1

Design of iRNA Molecule Mid-Cir Targeting Survivin and Bcl-2

Cell apoptosis suppressor gene Survivin and Bcl-2 are high expression widely in suppressor gene. The study found that, tumor cells growth can be suppressed through the inhibition of Survivin or Bcl-2 gene over-expression in tumor cells. The targeted siRNA can be used for cancer therapy through Survivin or Bcl-2 gene expression inhibition.

Design of iRNA molecule Mid-Cir, which contains a sense and antisense strand, the 3' segment of antisense strand target an mRNA that encodes Survivin gene, the 5' segment of antisense strand target an mRNA that encodes Bcl-2 gene, and the structure Mid-Cir of shown in FIG. 1.

SEQ ID NO: 1 shows a sense sequence of an iRNA Mid-Cir.

Sense strand:
(SEQ ID NO: 1)
5'-GACUUGGCCCAGUGUUUCUUCAGGAUGACUGAGUACCUGAA-3'.

SEQ ID NO: 2 is an antisense sequence that complementary to a sense sequence of an iRNA Mid-Cir with non-complementary loop structure.

Antisense strand:
(SEQ ID NO: 2)
5'-UUCAGGUACUCAGUCAUCCGAGAGAAACACUGGGCCAAGUC-3'.

The control siRNAs: 1) Sur-2 is the siRNA that target Survivin gene, the sense sequence is the 1~19 nucleotides from 5'end of SEQ ID NO: 1, antisense sequence is the 1~19 nucleotides from 3'end of SEQ ID NO: 1. 2) Bcl-1 is the siRNA that target Bcl-2 gene, the sense sequence is the 1~19 nucleotides from 3'end of SEQ ID NO: 2, antisense sequence is the 1~19 nucleotides from 5'end of SEQ ID NO: 2.

Example 2

Design of iRNA Molecule Mid-Loop Targeting Survivin and Bcl-2

Cell apoptosis suppressor gene Survivin and Bcl-2 are high expression widely in suppressor gene. The study found that, tumor cells growth can be suppressed through the inhibition of Survivin or Bcl-2 gene over-expression in tumor cells. The targeted siRNA can be used for cancer therapy through Survivin or Bcl-2 gene expression inhibition.

Design of iRNA molecule Mid-Loop, which contains a sense and antisense strand, the 3' segment of antisense strand target an mRNA that encodes Survivin gene, the 5' segment of antisense strand target an mRNA that encodes Bcl-2 gene, and the structure of Mid-Loop shown in FIG. 2.

SEQ ID NO: 3 shows a sense sequence of an iRNA Mid-Loop.

Sense strand:
(SEQ ID NO: 3)
5'-GACUUGGCCCAGUGUUUCUCAUGCGUCGGGAUGACUGAGUACCUG
AA-3'.

SEQ ID NO: 4 is an antisense sequence that complementary to a sense sequence of an iRNA Mid-Loop with self-complementary looped nucleotide hairpin structure.

Antisense strand:
(SEQ ID NO: 4)
5'-UUCAGGUACUCAGUCAUCCGCAGCACACAGAAACACUGGGCCAAG
UC-3'.

The control siRNAs: 1) Sur-2 is the siRNA that target Survivin gene, the sense sequence is the 1~19 nucleotides from 5'end of SEQ ID NO: 1, antisense sequence is the 1~19 nucleotides from 3'end of SEQ ID NO: 1. 2) Bcl-1 is the siRNA that target Bcl-2 gene, the sense sequence is the 1~19 nucleotides from 3'end of SEQ ID NO: 2, antisense sequence is the 1~19 nucleotides from 5'end of SEQ ID NO: 2.

Example 3

Design of iRNA Molecule By-Pass Targeting Survivin and Bcl-2

Cell apoptosis suppressor gene Survivin and Bcl-2 are high expression widely in suppressor gene. The study found that, tumor cells growth can be suppressed through the inhibition of Survivin or Bcl-2 gene over-expression in tumor cells. The targeted siRNA can be used for cancer therapy through Survivin or Bcl-2 gene expression inhibition.

Design of iRNA molecule By-Pass, which contains a sense and two antisense strand: antisense strand 1 and antisense strand 2, the 3' and 5' segment of antisense strand 1 target an mRNA that encodes Survivin gene, the 5' segment of antisense strand 2 target an mRNA that encodes Bcl-2 gene, and the 3' segment of antisense strand 2 target an mRNA that encodes Bcl-2 gene, and the structure of By-Pass shown in FIG. 3.

SEQ ID NO: 5 shows a sense sequence of an iRNA By-Pass.

```
Sense strand:
                                      (SEQ ID NO: 5)
5'-GACUUGGCCCAGUGUUUCUCAUGCGUCGGGAUGACUGAGUACCUG

AA-3'.
```

SEQ ID NO: 6 is the antisense strand 1 that 3' segment is complementary to the 5' segment of SEQ ID NO: 5, SEQ ID NO: 7 is the antisense strand 2 that 5' segment is complementary to the 3' segment of SEQ ID NO: 5, the 5' segment of SEQ ID NO: 6 is complementary to the 5' segment of SEQ ID NO: 7.

```
Antisense strand 1:
                                      (SEQ ID NO: 6)
5'-UCCUUUCUGUCAAGAAGCAGUUCAGAAACACUGGGCCAAGUC-3'.

Antisense strand 2:
                                      (SEQ ID NO: 7)
5'-UUCAGGUACUCAGUCAUCCCAACUGCUUCUUGACAGAAAGGA-3'.
```

The control siRNAs: 1) Sur-2 is the siRNA that target Survivin gene, the sense sequence is the 1~19 nucleotides from 5'end of SEQ ID NO: 1, antisense sequence is the 1~19 nucleotides from 3'end of SEQ ID NO: 1. 2) Bcl-1 is the siRNA that target Bcl-2 gene, the sense sequence is the 1~19 nucleotides from 3'end of SEQ ID NO: 2, antisense sequence is the 1~19 nucleotides from 5'end of SEQ ID NO: 2.

Example 4

Real-Time Quantitative PCR (RT-qPCR) Detection the Silencing Effects of Survivin Target Gene by iRNA Molecules Mid-Cir, Mid-Loop, By-Pass.

Cell culture: SMMC-7721 cells are cultured in DMEM supplemented with 10% FBS (Gibco Inc.) at 37° C. supplied with 5% CO2.

Cell Plated and transfection: 1×105 cells/well were plated in a 96-well plate and grown in DMEM supplemented with 10% FBS (Gibco Inc.) at 37° C. supplied with 5% CO2 overnight. The procedure of transfection followed by Lipofectamin™2000 (Invitrogen Inc.) protocol. The concentrations of experimental RNA molecules were 10 nM/well.

The level of mRNA encoding Survivin was determined by RT-qPCR: the cell mRNAs were extracted by TurboCapture mRNA Kit (QIAGEN Inc.), the procedure followed by the protocol. 80 μl RNase free water was added to dissolve the RNA, and 4 μl RNA was took as template to RT-qPCR amplification.

The primers used to detect the level of Survivin gene by RT-qPCR were:

```
5' Forward primer:
                                      (SEQ ID NO: 8)
ACCGCATCTCTACATTCAAG, 3' Reverse primer:
                                      (SEQ ID NO: 9)
CAAGTCTGGCTCGTTCTC.
```

The level of mRNA encoding Survivin was determined by RT-qPCR, meanwhile GAPDH was determined as the loading control, and 3 repeat reactions were set up per sample. The 25 μl reaction mix contained: 4 μl template RNA, 12.5 μl of 2×SensiMix One-Step (Quantance), 1 μl 5' forward and 3' reverse primer (10 μM), 0.5 μl 50×SYBR Green I and added RNase free water to 25 μl. The reaction was repeated for 45 cycles as reverse transcription at 42° C. for 30 min, preheating at 95° C. for 7 min, denaturing at 95° C. for 20 s, annealing at 60° C. for 30 s, and extension at 72° C. for 30 s.

Figure 4:
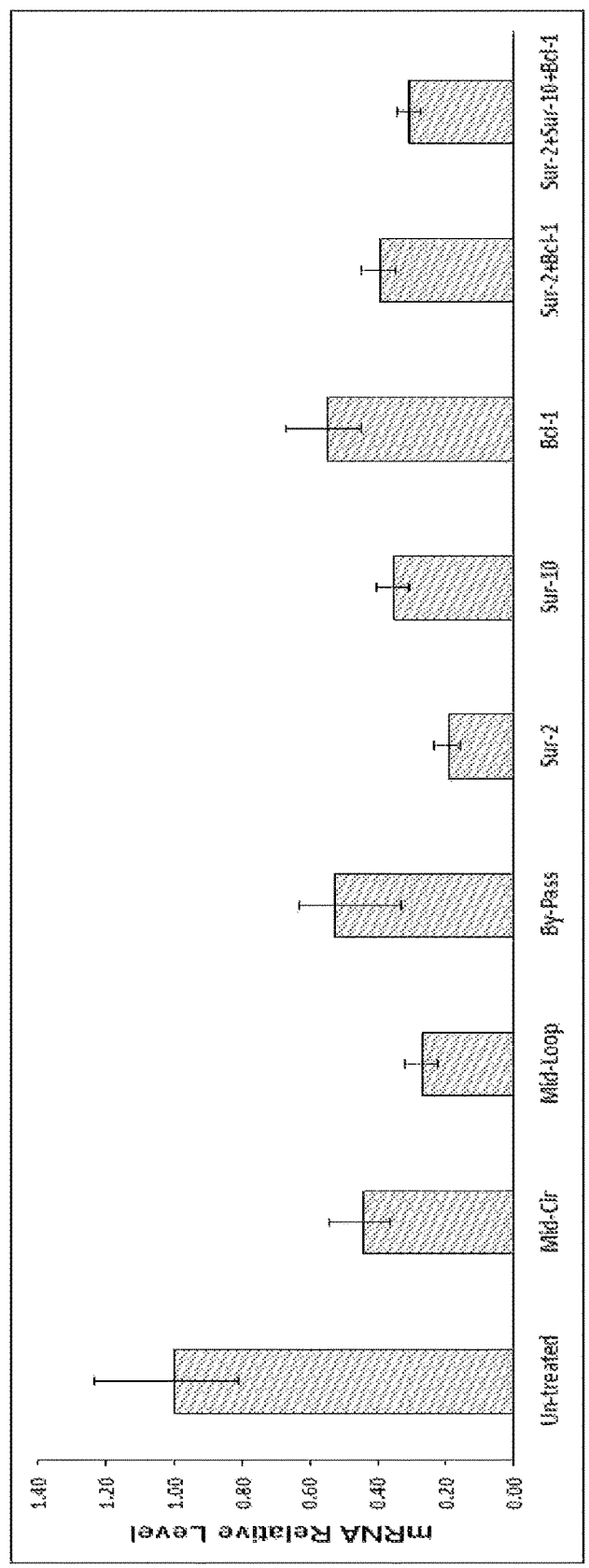
FIG. 4 shows the relative level of Survivin mRNA in SMMC-7721 hepatoma cells transfected with various iRNA. iRNA molecules Mid-Cir, Mid-Loop, By-Pass all had shown better results than the corresponding Sur-2 transfection group and Sur-2/Bcl-1 co-transfection group in Survivin gene silencing.

As shown in FIG. 4, the results were analyzed by 2-ΔΔCt methods of histogram. The iRNA molecules Mid-Cir, Mid-Loop, By-Pass all had shown the better results than the corresponding Sur-2 transfection group and Sur-2/Bcl-1 co-transfection group in the Survivin gene silencing.

Example 5

RT-qPCR Detection the Silencing Effects of Bcl-2 Target Gene by iRNA Molecules Mid-Cir, Mid-Loop, By-Pass.

Cell culture: SMMC-7721 cells are cultured in DMEM supplemented with 10% FBS (Gibco Inc.) at 37° C. supplied with 5% CO2.

Cell Plated and transfection: 1×105 cells/well were plated in a 96-well plate and grown in DMEM supplemented with 10% FBS (Gibco Inc.) at 37° C. supplied with 5% CO2 overnight. The procedure of transfection followed by Lipofectamin™2000 (Invitrogen Inc.) protocol. The concentrations of experimental RNA molecules were 10 nM/well.

The level of mRNA encoding Bcl-2 was determined by RT-qPCR: the cell mRNAs were extracted by TurboCapture mRNA Kit (QIAGEN Inc.), the procedure followed by the protocol. 80 μl RNase free water was added to dissolve the RNA, and 4 μl RNA was took as template to RT-qPCR amplification.

The primers used to detect the level of Bcl-2 gene by RT-qPCR were:

```
5' Forward primer:
                                      (SEQ ID NO: 10)
GGCTGGGATGCCTTTGTG, 3' Reverse primer:
                                      (SEQ ID NO: 11)
GCCAGGAGAAATCAAACAGAGG.
```

The level of mRNA encoding Bcl-2 was determined by RT-qPCR, meanwhile GAPDH was determined as the loading control, and 3 repeat reactions were set up per sample. The 25 µL reaction mix contained: 4 µl template RNA, 12.5 µl of 2×SensiMix One-Step (Quantance), 1 µl 5' forward and 3' reverse primer (10 µM), 0.5 µl 50×SYBR Green I and added RNase free water to 25 µl. The reaction was repeated for 45 cycles as reverse transcription at 42° C. for 30 min, preheating at 95° C. for 7 min, denaturing at 95° C. for 20 s, annealing at 60° C. for 30 s, and extension at 72° C. for 30 s.

Figure 5:
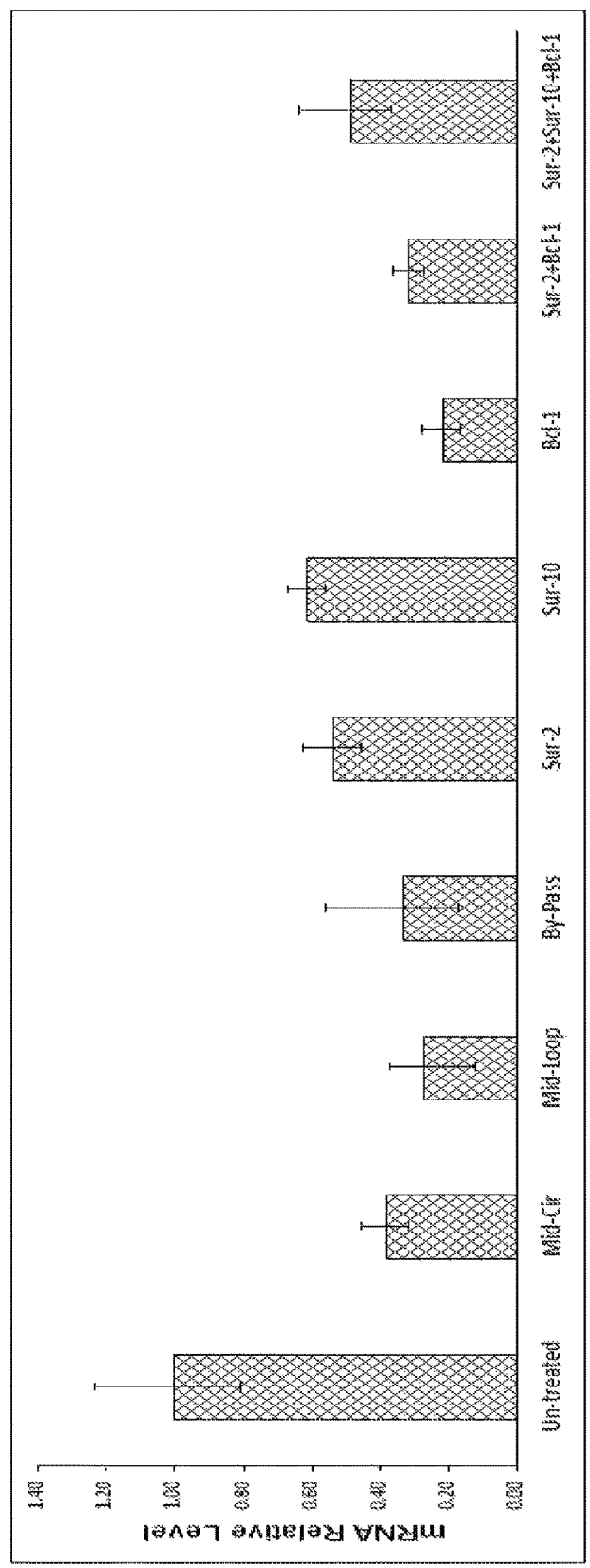
FIG. 5 shows the relative level of Bcl-2 mRNA in SMMC-7721 hepatoma cells transfected with various iRNA iRNA molecules Mid-Cir, Mid-Loop, By-Pass all had shown better results than the corresponding Bcl-1 transfection group and Sur-2/Bcl-1 co-transfection group in Bcl-2 gene silencing.

As shown in FIG. 5, the results were analyzed by 2-ΔΔCt methods of histogram. The iRNA molecules Mid-Cir, Mid-Loop, By-Pass all had shown the better results than the corresponding Bcl-1 transfection group and Sur-2/Bcl-1 co-transfection group in the Bcl-2 gene silencing.

Example 6

Interferon Response was Measured by RT-qPCR.

Cell culture: SMMC-7721 cells are cultured in DMEM supplemented with 10% FBS (Gibco Inc.) at 37° C. supplied with 5% CO2.

Cell Plated and transfection: 1×105 cells/well were plated in a 96-well plate and grown in DMEM supplemented with 10% FBS (Gibco Inc.) at 37° C. supplied with 5% CO2 overnight. The procedure of transfection followed by Lipofectamin™2000 (Invitrogen Inc.) protocol. The concentrations of experimental RNA molecules were 10 nM/well.

The level of mRNA encoding interferon-related gene OAS1 was determined by RT-qPCR: the cell mRNAs were extracted by TurboCapture mRNA Kit (QIAGEN Inc.), the procedure followed by the protocol. 80 µl RNase free water was added to dissolve the RNA, and 4 µl RNA was took as template to RT-qPCR amplification.

The primers used to detect the level of interferon-related gene OAS1 by RT-qPCR were:

```
5' Forward primer:
                                (SEQ ID NO: 12)
GTGAGCTCCTGGATTCTGCT, 3' Reverse primer:
                                (SEQ ID NO: 13)
TGTTCCAATGTAACCATATTTCTGA.
```

The level of mRNA encoding OAS1 was determined by RT-qPCR, meanwhile GAPDH was determined as the loading control, and 3 repeat reactions were set up per sample. The 25 µL reaction mix contained: 4 µl template RNA, 12.5 µl of 2×SensiMix One-Step (Quantance), 1 µl 5' forward and 3' reverse primer (10 µM), 0.5 µl 50×SYBR Green I and added RNase free water to 25 µl. The reaction was repeated for 45 cycles as reverse transcription at 42° C. for 30 min, preheating at 95° C. for 7 min, denaturing at 95° C. for 20 s, annealing at 60° C. for 30 s, and extension at 72° C. for 30 s.

Figure 6:
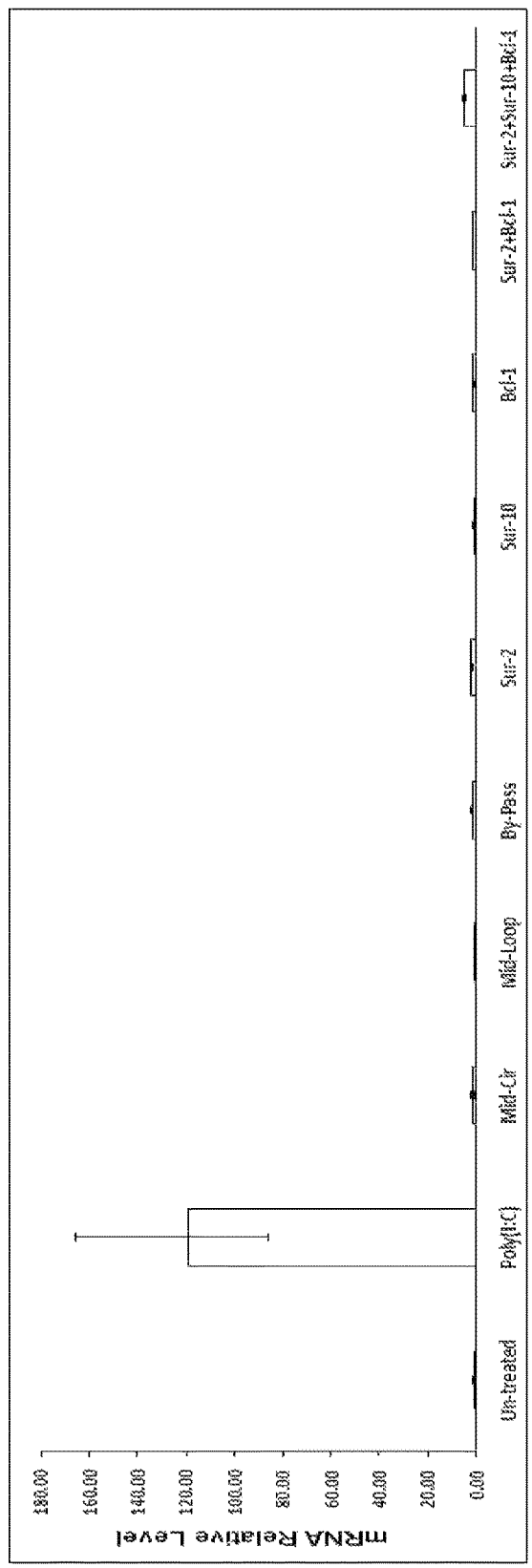
FIG. 6 shows the relative level of OAS1 mRNA in SMMC-7721 hepatoma cells transfected with various iRNA. Comparisons with the normal group, the mRNA expression level of OAS1 gene in the positive control group was increased significantly; the OAS1 gene of other group did not have high level mRNA expression. The results indicated that the iRNA molecules Mid-Cir, Mid-Loop, By-Pass did not induce interferon response.

As shown in FIG. 6, the results were analyzed by 2-ΔΔCt methods of histogram. During experiment, 5 ng/well Polyinosine-polycytidylic acid (Poly(I:C)) were transfected as positive control. Poly(I:C) is a synthetic analog of double-stranded RNA (dsRNA), a molecule pattern associated with viral infection, and it can induce antimicrobial immune responses. Comparisons with the normal group, the mRNA of OAS1 gene in positive control group were step-up significantly; the OAS1 gene of other group had no high expression. The results indicated the iRNA molecules Mid-Cir, Mid-Loop, By-Pass had not induced the interferon response.

Example 7

The Mid-Cir, Mid-Loop, By-Pass Inhibition Rates of SMMC-7721 Cells were Detected by CCK-8.

Cell culture: SMMC-7721 cells are cultured in DMEM supplemented with 10% FBS (Gibco Inc.) at 37° C. supplied with 5% CO2.

Cell Plated and transfection: 1×105 cells/well were plated in a 96-well plate and grown in DMEM supplemented with 10% FBS (Gibco Inc.) at 37° C. supplied with 5% CO2 overnight. The procedure of transfection followed by Lipofectamin™2000 (Invitrogen Inc.) protocol. The concentrations of experimental RNA molecules were 10 nM/well.

CCK-8 detection: 1/10 volume CCK-8 solution (Dojindo) of medium were added per well. Then, cells were keep incubation in cell culture oven for 0.5~4 h. The absorbance values were measured at 450 nm wave-length by microplate reader (Bio-Rad).

Figure 7:
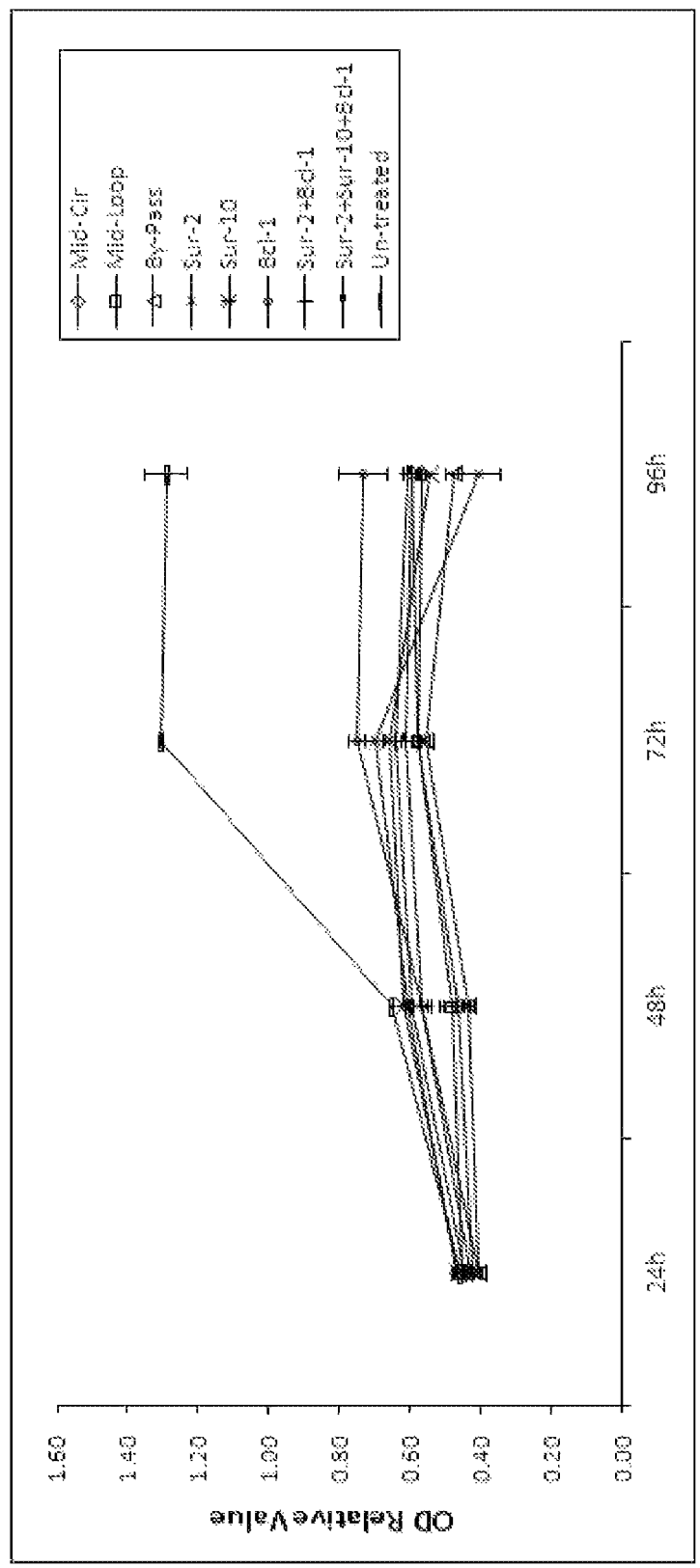
FIG. 7 shows the growth curve of SMMC-7721 hepatoma cells.
Figure 8:
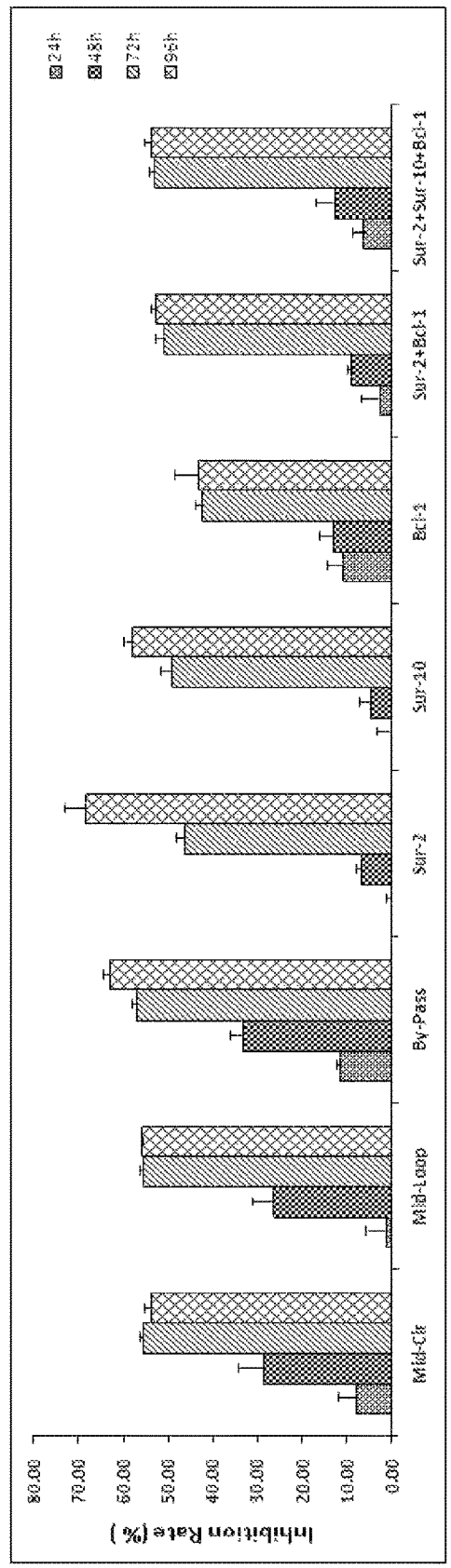
FIG. 8 shows inhibition of SMMC-7721 hepatoma cell growth by different RNA molecules. The results show that hepatoma cells were inhibited significantly after the treatment of the iRNA molecules Mid-Cir, Mid-Loop, By-Pass for 48 hrs, 72 hrs, 96 hrs.

As shown in FIG. 7, the growth curve was made according to the A450 values. The histogram was shown in FIG. 8, the cell growth inhibition rates were calculated according to the formula: cell proliferation rate=(1−A450 mean value per group/A450 mean value of control group)×100%. The results show that the hepatoma cells were inhibited significantly after the treatment of the iRNA molecules Mid-Cir, Mid-Loop, By-Pass for 48 hrs, 72 hrs, 96 hrs.

Example 8

The Mid-Cir, Mid-Loop, By-Pass Inhibition Rates of HepG2 Cells were Detected by CCK-8.

Cell culture: HepG2 cells are cultured in DMEM supplemented with 10% FBS (Gibco Inc.) at 37° C. supplied with 5% CO2.

Cell Plated and transfection: 1×105 cells/well were plated in a 96-well plate and grown in DMEM supplemented with 10% FBS (Gibco Inc.) at 37° C. supplied with 5% CO2 overnight. The procedure of transfection followed by Lipofectamin™2000 (Invitrogen Inc.) protocol. The concentrations of experimental RNA molecules were 10 nM/well.

CCK-8 detection: 1/10 volume CCK-8 solution (Dojindo) of medium were added per well. Then, cells were keep incubation in cell culture oven for 0.5~4 h. The absorbance values were measured at 450 nm wave-length by microplate reader (Bio-Rad).

Figure 9:
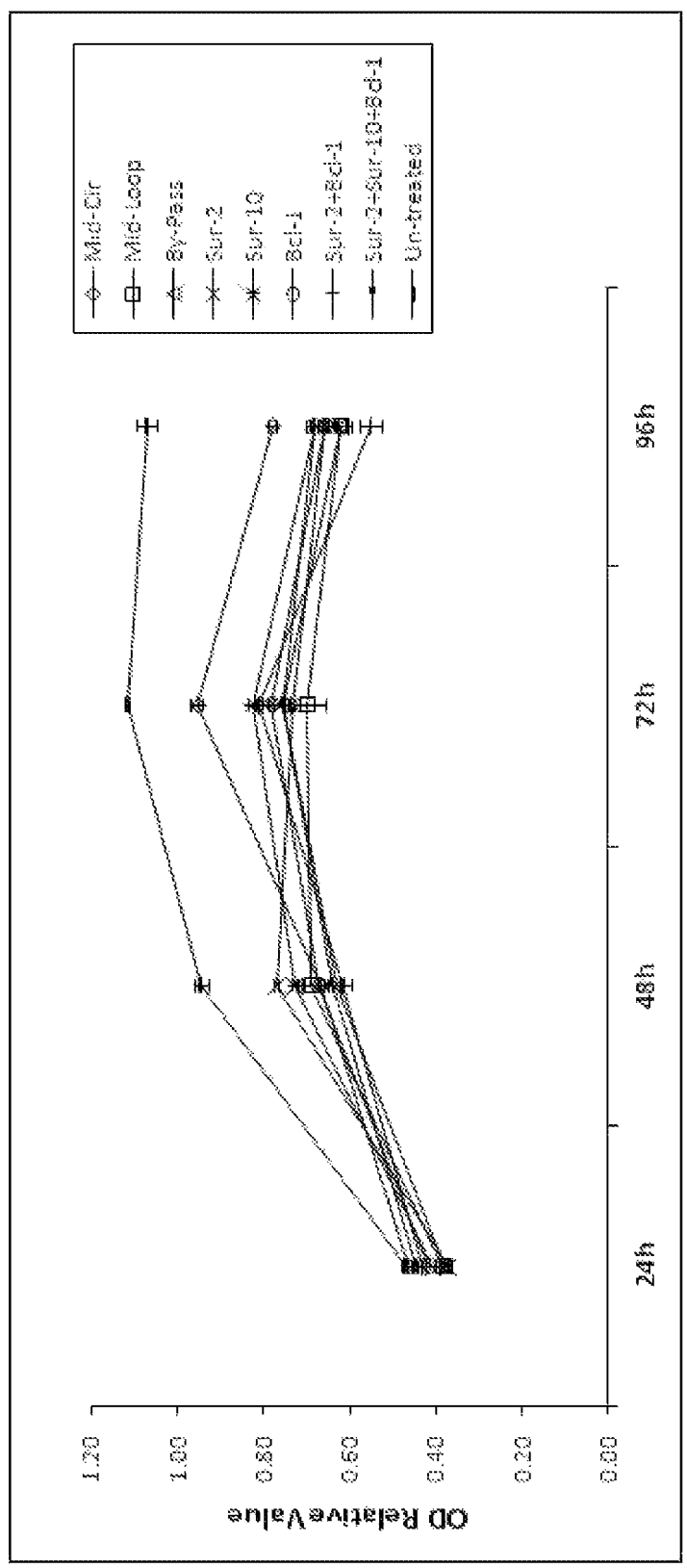
FIG. 9 shows the growth curve of HepG2 hepatoma cells.
Figure 10:
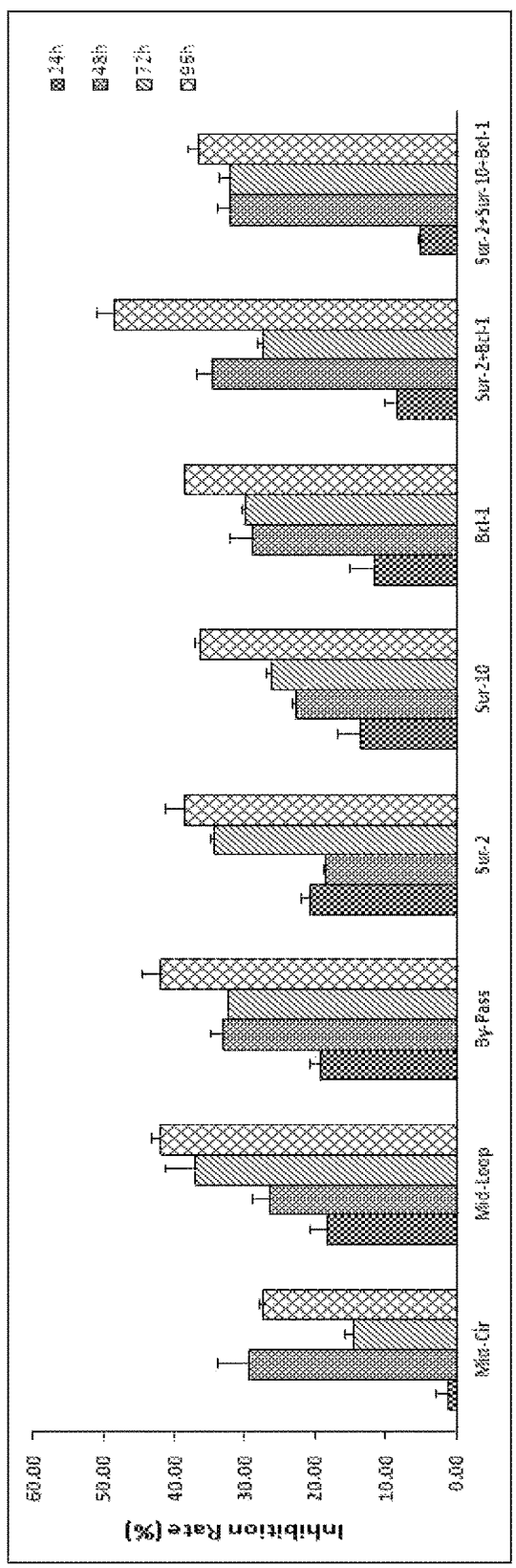
FIG. 10 shows inhibition of HepG2 hepatoma cell growth by different RNA molecules. The results show that the hepatoma cells were inhibited significantly after the treatment of the iRNA molecules Mid-Cir, Mid-Loop, By-Pass for 48 hrs, 72 hrs, 96 hrs.

As shown in FIG. 9, the growth curve was made according to the A450 values. The histogram was shown in FIG. 10, the cell growth inhibition rates were calculated according to the formula: cell proliferation rate=(1−A450 mean value per group/A450 mean value of control group)×100%. The results show that the hepatoma cells were inhibited significantly after the treatment of the iRNA molecules Mid-Cir, Mid-Loop, By-Pass for 48 hrs, 72 hrs, 96 hrs.

Example 9

In Vivo Gene Silencing Analysis

All procedures used in animal studies conducted at Alnylam are approved by the Institutional Animal Care and Use Committee (IACUC). The effects of the multi-targets iRNA molecules are validated in the mice bearing liver cancer via intratumoral injection. Liver tissue was dissolved in proteinase K-containing cell and tissue lysis buffer (Sigma) and subjected to tissue lysis with high shear forces. Total RNA was extracted with Qiagen RNA extraction kit. The expression levels of Bcl-2 and Survivin were determined by RT-qPCR. And the tumor inhibition rate is evaluated by the volumes of tumor and etc.

What is claimed is:

1. An interfering RNA (iRNA) molecule, comprising: a sense strand and an antisense strand annealed to said sense strand, wherein the sense strand and the antisense strand comprise the sequences of SEQ ID NOs: 3 and 4, respectively.

2. The iRNA of claim 1, wherein said iRNA comprises a sugar, base, or phosphate modification, or a combination thereof.

3. A pharmaceutical composition comprising the iRNA of claim 1, and a pharmaceutical acceptable excipient.

4. An interfering RNA (iRNA) molecule, comprising three non-continuous strands: a sense strand, a first antisense strand, and a second antisense strand, wherein
the sense strand, the first antisense strand, and the second antisense strand comprise the sequences of SEQ ID NOs: 5-7, respectively.

5. A pharmaceutical composition comprising the iRNA of claim 4, and a pharmaceutical acceptable excipient.

6. The iRNA of claim 4, wherein said iRNA comprises a sugar, base, or phosphate modification, or a combination thereof.

* * * * *